United States Patent
Majewski et al.

(10) Patent No.: US 8,003,947 B1
(45) Date of Patent: Aug. 23, 2011

(54) SYSTEM AND METHOD FOR MAGNITUDE AND PHASE RETRIEVAL BY PATH MODULATION

(75) Inventors: Alexander Majewski, Fairfield, CT (US); Rene Abreu, The Villages, FL (US)

(73) Assignee: Goodrich Corporation, Charlotte, NC (US)

( * ) Notice: Subject to any disclaimer, the term of this patent is extended or adjusted under 35 U.S.C. 154(b) by 2 days.

(21) Appl. No.: 12/712,736

(22) Filed: Feb. 25, 2010

(51) Int. Cl.
*G01N 21/17* (2006.01)

(52) U.S. Cl. ..................................... 250/360.1; 356/432

(58) Field of Classification Search ............... 250/336.1, 250/343, 347, 351, 360.1; 356/432, 436, 356/444
See application file for complete search history.

(56) References Cited

U.S. PATENT DOCUMENTS

| | | | |
|---|---|---|---|
| 2,779,230 | A | 1/1957 | White |
| 5,267,019 | A | 11/1993 | Whittaker et al. |
| 5,818,578 | A | 10/1998 | Inman et al. |
| 5,883,518 | A | 3/1999 | Borden |
| 5,903,358 | A | 5/1999 | Zare et al. |
| 5,966,019 | A | 10/1999 | Borden |
| 6,348,683 | B1 | 2/2002 | Verghese et al. |
| 6,466,322 | B1 | 10/2002 | Paldus et al. |
| 6,486,474 | B1 | 11/2002 | Owen et al. |
| 6,500,618 | B1 | 12/2002 | Woolard et al. |
| 6,865,198 | B2 | 3/2005 | Taubman |
| 7,174,037 | B2 | 2/2007 | Arnone et al. |
| 7,271,594 | B2 | 9/2007 | Abreu et al. |
| 7,291,839 | B1 | 11/2007 | Demers et al. |
| 7,352,463 | B2 | 4/2008 | Bounaix |
| 2002/0067480 | A1 | 6/2002 | Takahashi |
| 2004/0114939 | A1 | 6/2004 | Taylor |
| 2008/0049233 | A1* | 2/2008 | De Groot ..................... 356/511 |

FOREIGN PATENT DOCUMENTS

| WO | WO 03/005510 A1 | 1/2003 |
|---|---|---|
| WO | WO 2004/083796 A1 | 9/2004 |

OTHER PUBLICATIONS

Armerding, W. et al., *Multipass Optical Absorption Spectroscopy: a Fast-Scanning Laser Spectrometer for the in situ Determination of Atmospheric Trace-Gas Components, in Particular OH*, Applied Optics, vol. 35, No. 21, (1996), pp. 4206-4219.

Auton, J. P., *Infrared Transmission Polarizers by Photolithography*, Applied Optics, vol. 6, No. 6, (1967), pp. 1023-1027.

Blickensderfer, R. P. et al., *A Long Path, Low Temperature Cell*, Applied Optics, vol. 7, No. 11, (1968), pp. 2214-2217.

(Continued)

*Primary Examiner* — David P Porta
*Assistant Examiner* — Mark R Gaworecki
(74) *Attorney, Agent, or Firm* — Alston & Bird LLP

(57) ABSTRACT

A system includes a transmitter is configured to transmit an electromagnetic signal through a sample cell (including a sample medium) to a receiver, which is configured to receive the electromagnetic signal and another electromagnetic signal for mixing therewith. Propagation paths of the signals to the transmitter and receiver include a first propagation path of the electromagnetic signal to the transmitter, and a second propagation path of the other electromagnetic signal to the receiver. The arrangement, which is located along either or each of the propagation paths of signals to the transmitter and receiver, is configured to alter the length of a respective propagation path. And the processor configured to recover an amplitude and phase of the transmitted electromagnetic signal, and calculate a complex index of refraction of the sample medium as a function of the amplitude and phase of the transmitted electromagnetic signal.

20 Claims, 5 Drawing Sheets

OTHER PUBLICATIONS

Brown, E. R. et al., *Coherent Millimeter-Wave Generation by Heterodyne Conversion in Low-Temperature-Grown GaAs Photoconductors*, J. Appl. Phys., 73(3), (1993), pp. 1480-1484.

Edwards, T. H., *Multiple-Traverse Absorption Cell Design*, Journal of the Optical Society of America, vol. 51, No. 1, (1961), pp. 98-102.

Engel, G. S. et al., *Precise Multipass Herriott Cell Design: Derivation of Controlling Design Equations*, Optics Letters, vol. 32, No. 5, (2007), pp. 704-706.

Engeln, R. et al., *Phase Shift Cavity Ring Down Absorption Spectroscopy*, Chemical Physics Letters, 262, (1996), pp. 105-109.

Gregory, I. S. et al., *Resonant Dipole Antennas for Continuous-Wave Terahertz Photomixers*, [online] [retrieved May 24, 2010]. Retrieved from the Internet: <URL: http://adsabs.harvard.edu/abs/2004ApPhL..85.1622G>. 1 page.

Harmon, S. A. et al., *Part-Per-Million Gas Detection From Long-Baseline THz Spectroscopy*, Applied Physics Letters, vol. 85, No. 11, (2004), pp. 2128-2130.

Hayden, A. et al., *Determination of Trace-Gas Amounts in Plumes by the Use of Orthogonal Digital Filtering of Thermal-Emission Spectra*, Applied Optics, vol. 35, No. 16, (1996), pp. 2802-2809.

Herbelin, J. M. et al., *Sensitive Measurement of Photon Lifetime and True Reflectances in an Optical Cavity by a Phase-Shift Method*, Applied Optics, vol. 19, No. 1, (1980), pp. 144-147.

Lehmann, K. K. et al., *The Superposition Principle and Cavity Ring-Down Spectroscopy*; J. Chem. Phys., vol. 105, No. 23, (1996), pp. 10263-10277.

McCubbin, Jr., T. K. et al., *A White-Type Multiple-Pass Absorption Cell of Simple Construction*, Applied Optics, vol. 2, No. 7, (1963), pp. 764-765.

Mouret, G. et al., *THz Media Characterization by Means of Coherent Homodyne Detection, Results and Potential Applications*, Appl. Phys., B89, (2007), pp. 395-399.

Pickett, H. M. et al., *A New White Type Multiple Pass Absorption Cell*, Applied Optics, vol. 9, No. 10, (1970), pp. 2397-2398.

Rayl, G. J., *Multiple Traversal Absorption Cell of Minimum Volume: Design*, Applied Optics, vol. 15, No. 4, (1976), pp. 921-928.

Robert, C., *Simple, Stable, and Compact Multiple-Reflection Optical Cell for Very Long Optical Paths*, Applied Optics, vol. 46, No. 22, (2007), pp. 5408-5418.

Scherer, J. J. et al., *Cavity Ringdown Laser Absorption Spectroscopy: History, Development, and Application to Pulsed Molecular Beams*, Chem. Rev., 97, (1997), pp. 25-51.

Siegman, *11.5 Optical-Cavity Mode Frequencies*, Chapter 11: Laser Mirrors and Regenerative Feedback, pp. 435-437 (undated), (1986).

Ulrich, P. et al., *Variable Metal Mesh Coupler for Far Infrared Lasers*, Applied Optics, vol. 9, No. 11, (1970), pp. 2511-2516.

Verghese, S. et al., *Highly Tunable Fiber-Coupled Photomixers with Coherent Terahertz Output Power*, IEEE Transactions on Microwave Theory and Techniques, vol. 45, No. 8, (1997), pp. 1301-1309.

Verghese, S. et al., *Generation and Detection of Coherent Terahertz Waves Using Two Photomixers*, Applied Physics Letters, vol. 73, No. 26, (1998), pp. 3824-3826.

Verghese, S. et al., *The Photomixer Transceiver*, Invited Paper, SPIE Conference on Terahertz Spectroscopy and Applications, San Jose, CA, Jan. 1999, pp. 7-13.

White, J. U., *Very Long Optical Paths in Air*, J. Opt. Soc. Am., vol. 66, No. 5, (1976), pp. 411-416.

Zalicki, P. et al., *Cavity Ring-Down Spectroscopy for Quantitative Absorption Measurements*, J. Chem. Phys., 102 (7), (1995), pp. 2708-2717.

\* cited by examiner

SYSTEM AND METHOD FOR MAGNITUDE AND PHASE RETRIEVAL BY PATH MODULATION

FIELD OF THE INVENTION

Exemplary embodiments of present invention generally relate to systems and methods of propagating electromagnetic signals and, more particularly, systems and methods of magnitude and phase retrieval by path modulation.

BACKGROUND OF THE INVENTION

Spectrometry using continuous wave (CW) tunable sources with narrow spectral linewidth and long coherence lengths has well-known advantages associated with high spectral contrast, frequency selectivity and excellent sensitivity. Scanning CW terahertz (THz) spectrometers are a prime example of this technology. In such systems, phase stability in the transmitter-to-receiver demodulation processing may be required to obtain an accurate measurement of the transmitted electric-field intensity and to characterize any resulting absorption losses from samples in the spectrometer. However, spurious thermal and mechanical disturbances may undesirably generate variations in path length that modulate the received field intensity. It would therefore be desirable to design a system and method of controlling and modulating the path length to improve demodulation signal to noise ratio and stability.

SUMMARY OF THE INVENTION

In light of the foregoing background, embodiments of the present invention provide an improved system and method of magnitude and phase retrieval by path modulation. According to one aspect of the present invention, the system includes a transmitter configured to transmit an electromagnetic signal through a sample cell (including a sample medium and a base medium) to a receiver at each of one or more selectable frequencies, where the receiver is configured to receive the electromagnetic signal and another electromagnetic signal for mixing therewith. The system also includes an arrangement located along either of first or second propagation paths of signals to the transmitter or receiver, respectively, or along each of the first and second propagation paths, for altering the length of respective propagation path(s).

The system also includes a processor configured to recover an amplitude and phase of the transmitted electromagnetic signal, and configured to calculate a complex index of refraction of the sample medium as a function of the amplitude and phase of the transmitted electromagnetic signal. The processor may be configured to receive a sequence of samples of the received electromagnetic signal, and Discrete Fourier Transformation process the sequence of samples. In addition, the system may include a modulator configured to modulate the electromagnetic signal transmitted by the transmitter, where the modulator may be configured to modulate the electromagnetic signal at a frequency (e.g., $\omega_m$), which may be above the 1/f noise region of the receiver.

The arrangement is configured to alter the length of a respective propagation path such that the difference of the lengths of the first and second propagation paths is altered at a pre-selected rate during transmission of the electromagnetic signal from the transmitter to the receiver, and receipt of the electromagnetic signal and the other electromagnetic signal at the receiver. The arrangement may comprise a pair of arrangements each of which is located along a respective one of the first and second propagation paths. To effectuate an increase in the difference in the lengths of the first and second propagation paths at the pre-selected rate, one of the arrangements may be configured to increase the length of one of the propagation paths, while the other of the arrangements may be configured to decrease the length of the other of the propagation paths. The arrangement may include, for example, a spool and actuator. In such instances, an optical fiber propagation path may be wound about the spool, and the actuator may be configured to alter the diameter of the spool, and thereby alter the length of the respective propagation path.

The processor being configured to calculate a complex index of refraction of the sample medium may include being configured to calculate a real part $n_s$ and an imaginary part k of the complex index of refraction. The real part of the complex index of refraction may be calculated as a function of the recovered phase $\phi_{SAMPLE}$ of the transmitted electromagnetic signal, and as a function of a recovered phase $\phi_{REF}$ of an electromagnetic signal transmitted through the sample cell including the base medium but without the sample medium. Similarly, the imaginary part of the complex index of refraction may be calculated as a function of the recovered amplitude $E_s$ of the transmitted electromagnetic signal, and as a function of a recovered amplitude $E_o$ of an electromagnetic signal transmitted through the sample cell including the base medium but without the sample medium. For example, the real part of the complex index of refraction may be calculated according to the following:

$$n_s = (\phi_{REF} - \phi_{SAMPLE}) \times \frac{\lambda}{2\pi \times L_s} + n_o$$

where $\lambda$ (e.g., $\lambda_{THz}$) represents a wavelength of the transmitted electromagnetic signal, $L_s$ represents a propagation path length through the sample medium, and $n_o$ represents the free-space index of refraction. And the imaginary part of the complex index of refraction may be calculated according to the following:

$$k = -\frac{\lambda}{2\pi L_s} \ln\left(\frac{E_s}{E_o}\right)$$

The pre-selected rate may comprise a rate selected as a function of the frequency at which the electromagnetic signal is transmitted. More particularly, the pre-selected rate may comprise a rate selected to span one or more wavelengths of the electromagnetic signal transmitted at a respective frequency over a dwell time. In one instance, for example, the pre-selected rate may comprise a rate $\omega_{FS}$ selected to effectuate a path length modulation at a frequency:

$$\omega_{FS} = \frac{2\pi}{\lambda} n_F S_F$$

In the preceding, $n_F$ represents the index of refraction of a propagating medium of the propagation paths, and $S_F$ represents the pre-selected rate. In this regard, the processor may be configured to DFT process the sequence of samples at a first frequency of interest $\omega_m - \omega_{FS}$, and DFT process the sequence of samples at a second frequency of interest $\omega_m + \omega_{FS}$. And as the pre-selected rate may comprise a rate selected as a function of frequency, the pre-selected rate may comprise a rate selected for each of the one or more selectable frequencies, where the rate selected for one of the frequencies may differ from the rate selected for another of the frequencies.

According to other aspects of the present invention, a method of magnitude and phase retrieval by path modulation is provided. Exemplary embodiments of the present invention therefore provide an improved system and method of magnitude and phase retrieval by path modulation. As indicated above, and explained below, exemplary embodiments of the present invention may solve problems identified by prior techniques and provide additional advantages.

BRIEF DESCRIPTION OF THE DRAWINGS

Figure 1:
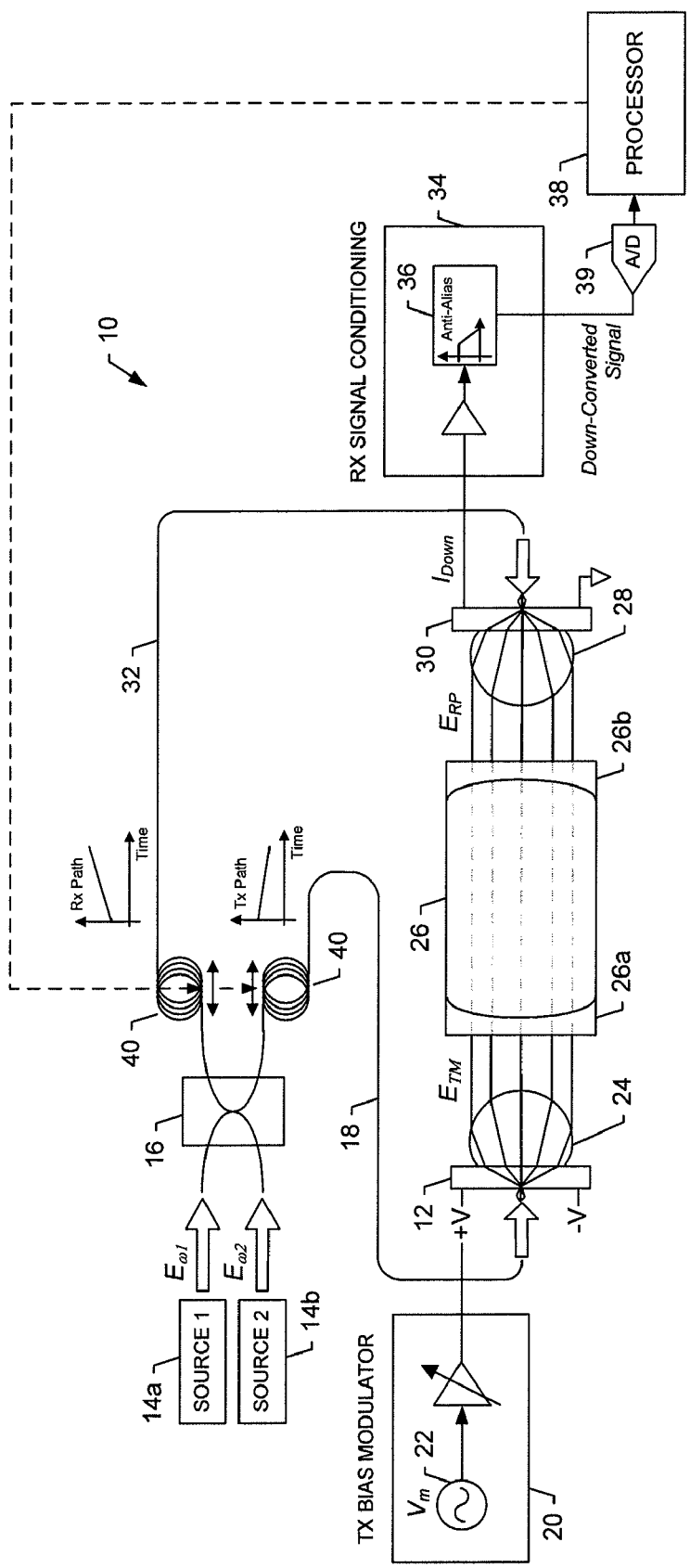
Figure 2:
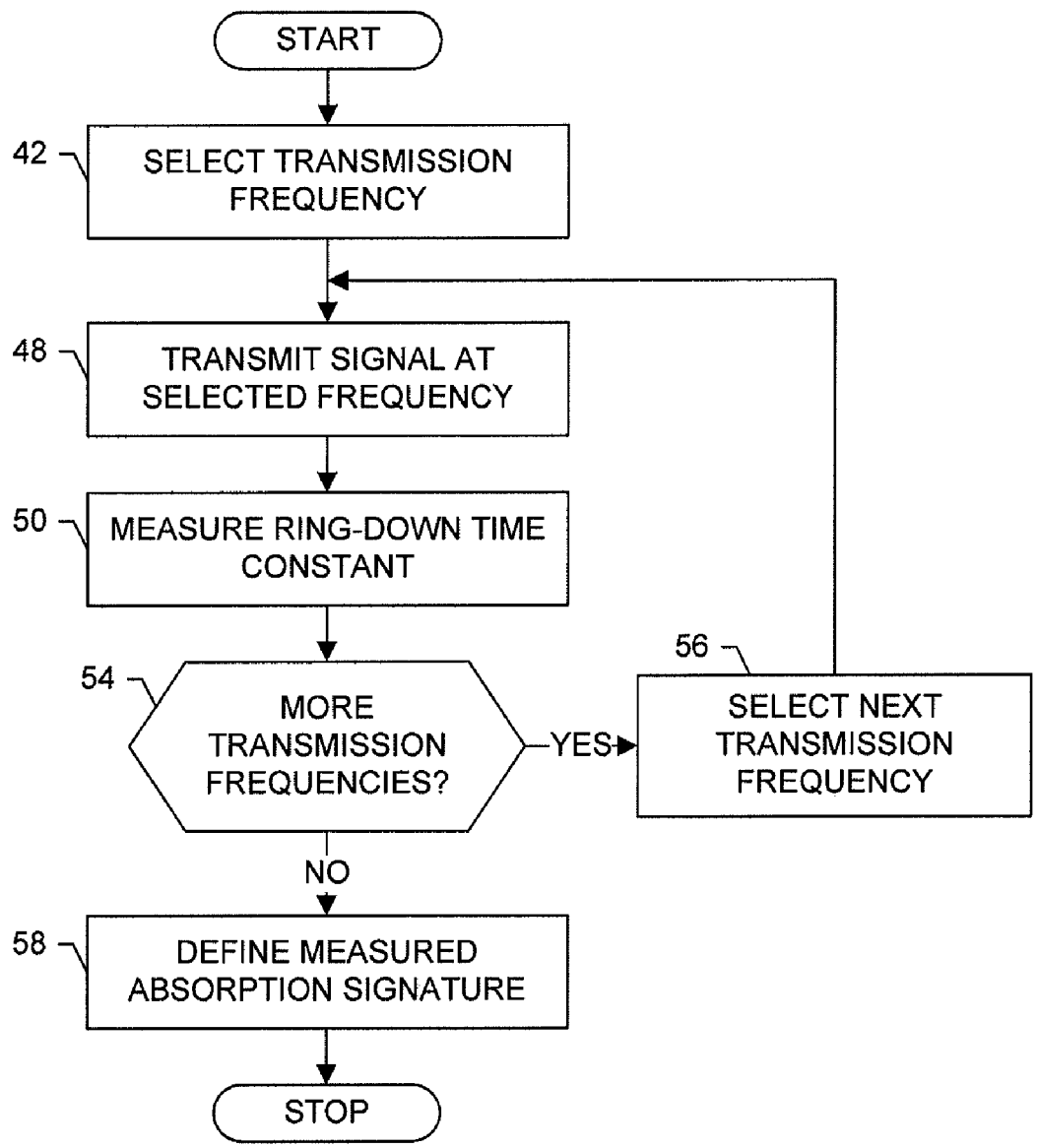
Figure 3:
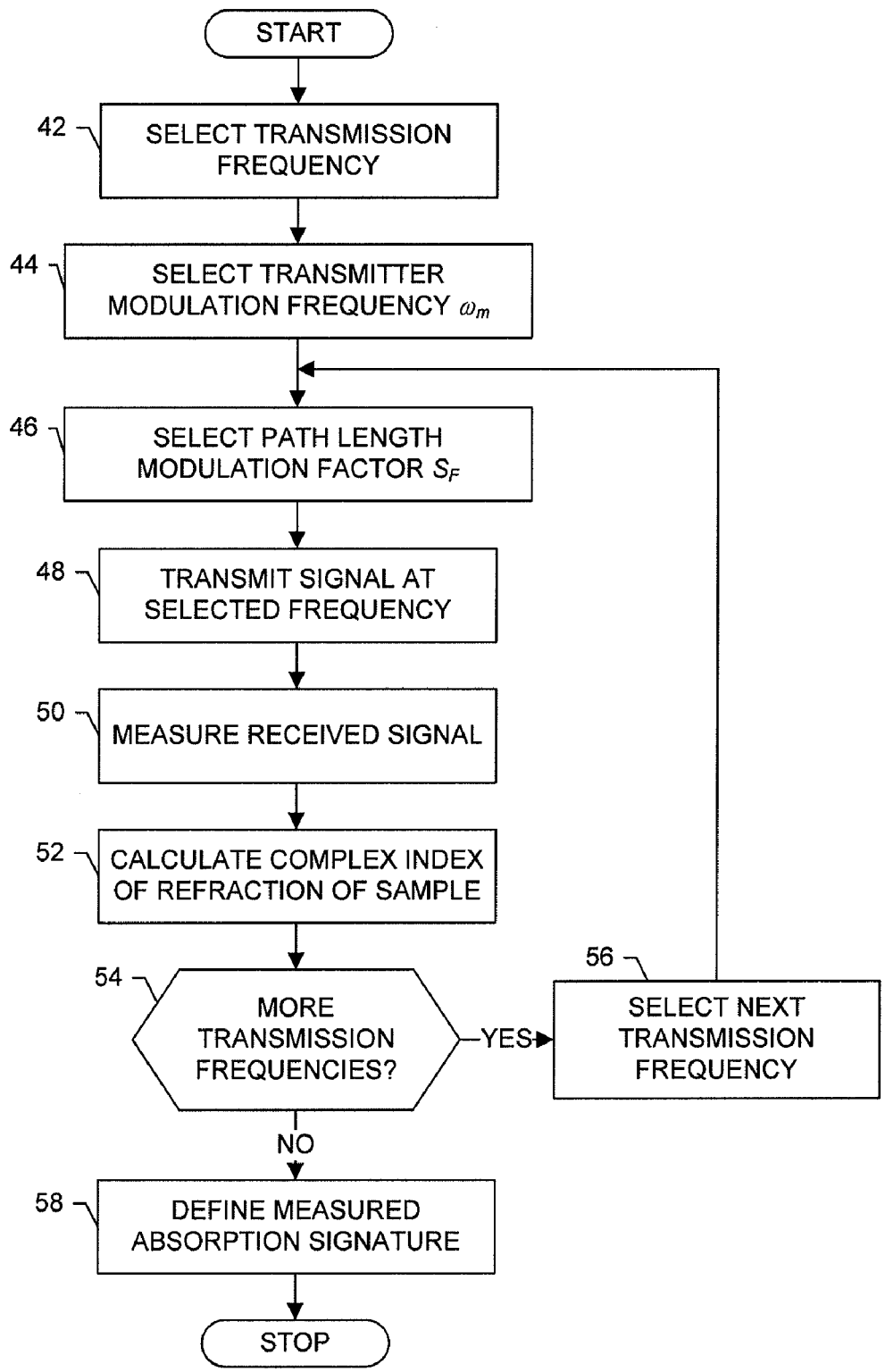
Figure 4:
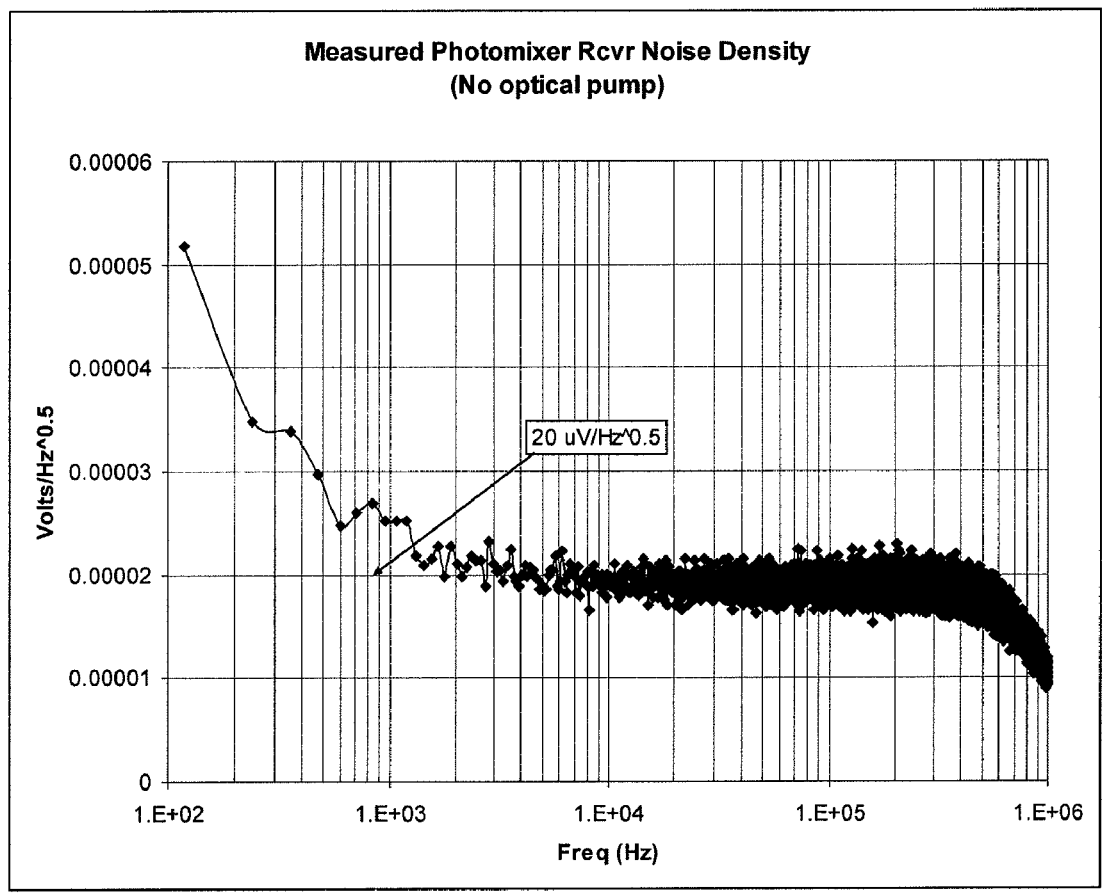
Figure 5:
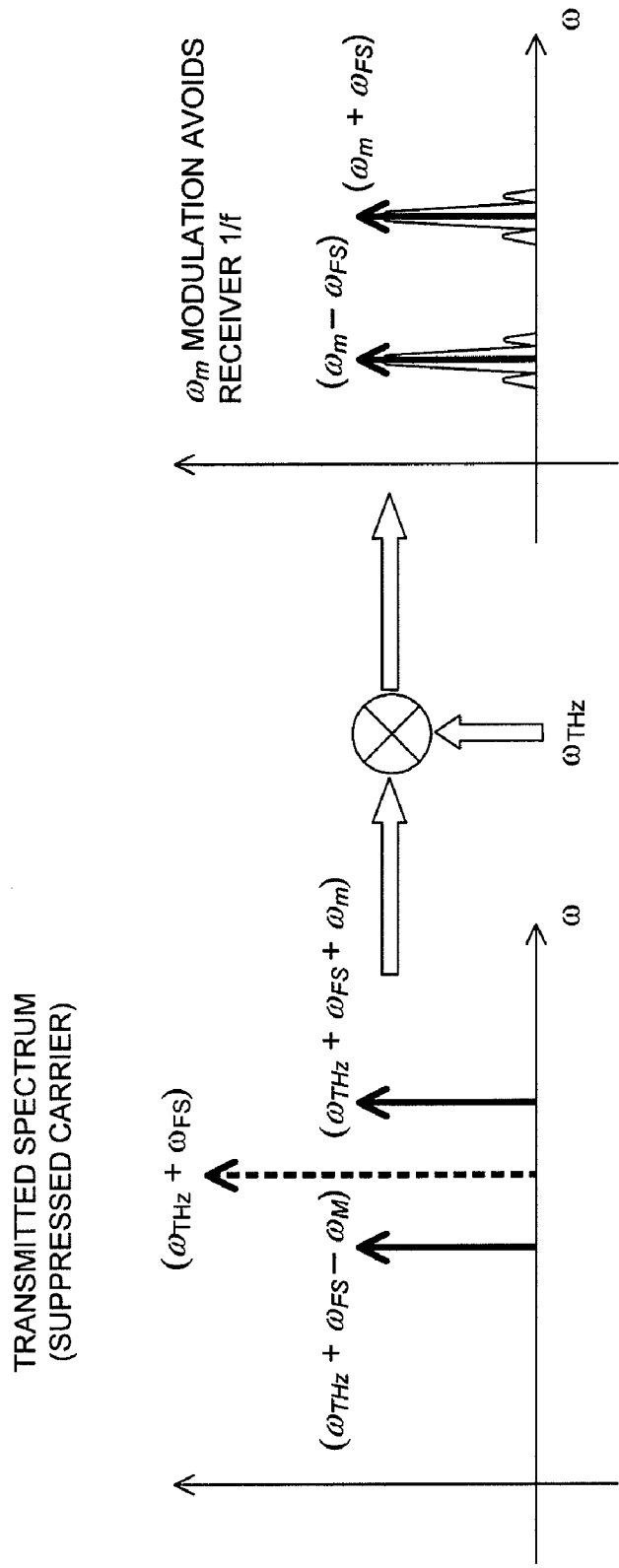

Having thus described the invention in general terms, reference will now be made to the accompanying drawings, which are not necessarily drawn to scale, and wherein:

FIG. 1 is a schematic block diagram of a spectrometer system in accordance with one exemplary embodiment of the present invention;

FIGS. 2 and 3 are flowcharts illustrating various steps in methods of sweeping a spectrometer system through a frequency spectrum, according to exemplary embodiments of the present invention;

FIG. 4 is a graph illustrating the measured noise density spectrum of a photomixer receiver, according to exemplary embodiments of the present invention; and FIG. 5 illustrates spectral diagrams illustrating frequency down conversion in the receiver of exemplary embodiments of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In this regard, reference may be made herein to a number of mathematical or numerical expressions that may be related by equality. It should be understood, however, that this equality may refer to an absolute or approximate equality, such that exemplary embodiments of the present invention may account for variations that may occur in the system and method, such as those due to engineering tolerances. Further, although a number of variables may be reflected by mathematical symbols including subscripts at various instances, it should be understood that these symbols and subscripts are presented solely for illustrative purposes, and should not be construed as limiting the scope of the invention. Like numbers refer to like elements throughout.

FIGS. 1 and 2 illustrate a spectrometer system and method that may benefit from exemplary embodiments of the present invention ("exemplary" as used herein referring to "serving as an example, instance or illustration"). It should be understood, however, that the spectrometer system and method illustrated and hereinafter described are merely illustrative of one type of system and method that may benefit from exemplary embodiments of the present invention and, therefore, should not be taken to limit the scope of the present invention. In this regard, while several embodiments of the spectrometer system and method are illustrated and will be hereinafter described for purposes of example, other types of systems and methods of propagating electromagnetic signals may readily employ the present invention. Moreover, the system and method of the present invention will be primarily described in conjunction with signals in the THz (or mmW) region of the electromagnetic spectrum. But the system and method of embodiments of the present invention may be utilized in conjunction with a variety of other applications, both within and outside the THz region of the electromagnetic spectrum.

As shown, a spectrometer system 10 of one exemplary embodiment of the present invention includes a transmitter 12 configured to transmit a beam of coherent radiation (electromagnetic wave) at a given frequency. The transmitter can comprise any of a number of different transmitters known to those skilled in the art. In one exemplary embodiment, for example, the transmitter comprises a photomixer transmitter. In such instances, the transmitter includes a high-speed photoconductive diode (i.e., photomixer), which may be pumped with two laser sources 14a, 14b via a beam combiner/splitter 16 and an optically coupled first optical path 18 (e.g., optical fiber). In this regard, the laser sources may be configured to emit signals with electric fields having offsetting frequencies at $\omega_1$ and $\omega_2$ (i.e., $E_{\omega 1}$ and $E_{\omega 2}$), which at the photomixer transmitter may be represented as follows:

$$E_{\omega 1} = E_1 \cos(\omega_1 t + \phi_{1T}) \tag{1}$$

$$E_{\omega 2} = E_2 \cos(\omega_2 t + \phi_{2T}) \tag{2}$$

where $E_1$ and $E_2$ represent the electric-field amplitudes of the beams from the first and second sources, respectively; and $\phi_{1T}$ and $\phi_{2T}$ represent phase constants introduced by virtue of propagation of the beams through the first optical path. Also note that frequencies $\omega_1$ and $\omega_2$ may be expressed as angular frequencies, or as corresponding temporal frequencies ($f = \omega / 2\pi$).

The inherently quadratic nature of the cross-gap absorption creates a difference (i.e., transmission) frequency (i.e., $\omega_2 - \omega_1$) in the photocurrent induced in the diode of the transmitter 12, where the corresponding electric field may be represented as follows:

$$E_T = \eta_T E_1 E_2 \cos(\omega_{THz} t + \phi_{12T}) \tag{3}$$

where $\eta_T$ represents the photomixer transmitter conversion efficiency, $\omega_{THz} = \omega_2 - \omega_1$, and $\phi_{12T} = \phi_{2T} - \phi_{1T}$. The transmitter 12 may be coupled to a transmitter bias modulator 20 including a voltage source 22 configured to generate a sinusoidal modulated voltage with which the photomixer of the transmitter may be biased, the modulator producing an electric field $E_M = V_m \cos(\omega_m t)$, although it should be understood that the system need not frequency modulate (at frequency $\omega_m$) the signal. By locating the photomixer at the driving point of an antenna, such as a spiral, dipole or slot antenna, the difference-frequency current is converted to difference-frequency photons. The result is a highly-tunable, continuous-wave (CW), highly-coherent source of radiation contained in a single (quasi-Gaussian) spatial mode, and having a transmitted electric field $E_{TM}$. This transmitted electric field may be represented as the product of $E_T$ and $E_M$, as follows:

$$E_{TM} = V_m \cos(\omega_m t) \eta_T E_1 E_2 \cos(\omega_{THz} t + \phi_T) \tag{4}$$

$$E_{TM} = \frac{V_m \eta_T E_1 E_2}{2} [\cos((\omega_{THz} + \omega_m)t + \phi_T) + \cos((\omega_{THz} - \omega_m)t + \phi_T)] \tag{5}$$

In equations (4) and (5), $\phi_T$ represents the sum of $\phi_{12T}$ and some phase delay related to the photomixer and antenna transfer function, which may be significant and may cause large signal variability when detected at a receiver. For more information on such a transmitter, see U.S. Pat. No. 6,348,683 entitled: Quasi-Optical Transceiver Having an Antenna with Time Varying Voltage, issued Feb. 19, 2002.

Thus, the method of one embodiment includes selecting a transmission frequency, thereafter transmitting a beam of radiation (i.e., source beam) at that frequency from the transmitter 12, as shown in blocks 42 and 48 of FIG. 2. The transmission frequency can be selected in any of a number of different manners. To detect a sample based upon a measured absorption signature, however, the transmission frequency may be typically selected within a range of frequencies over which the absorption signature is defined. In a photomixer transmitter, then, the photomixer can be pumped with tunable laser sources at a frequency $\omega_2$, and a frequency $\omega_1$ that are selected to thereby select the difference, or transmission, frequency (i.e., $\omega_2-\omega_1$).

The beam of radiation from the transmitter 12 may pass through a collimating lens 24 to produce a collimated beam of radiation. The beam may then pass through a sample cell 26 that may be bounded by reflectors 26a and 26b through which the beam passes, and that may include a sample medium to be analyzed and a base medium, such as ambient air. As will be appreciated, the sample and base medium can have any of a number of different forms through which the beam of radiation is at least partially transmissive. For example, the sample and base medium can comprise a solid, liquid, gas, plasma or aerosol. More particularly, in various advantageous embodiments, the base medium of ambient air may be in gas form, while a sample may be in gas or aerosol form.

As the beam of radiation passes through the sample cell 26, the sample and base medium in the sample cell absorb at least a portion of the beam, or more particularly at least a portion of the electric field of the beam. The remaining, unabsorbed portion of the beam of radiation (i.e., received signal) then exits the sample cell. The sample signal then propagates to a focusing lens 28, from which the focused signal is picked up or otherwise received by a receiver 30. This received signal $E_{RP}$, which may include an additional phase delay added during propagation of the signal from the transmitter 12 to the receiver, may be represented as follows:

$$E_{RP} = \frac{V_m \eta_T E_1 E_2}{2} \times e^{-2\pi k \frac{L}{\lambda_{THz}}} \times \begin{bmatrix} \cos\left((\omega_{THz} + \omega_m)t + \phi_T - 2\pi \frac{n \times L}{\lambda_{THz}}\right) + \\ \cos\left((\omega_{THz} - \omega_m)t + \phi_T - 2\pi \frac{n \times L}{\lambda_{THz}}\right) \end{bmatrix} \quad (6)$$

where L represents the propagation distance between the transmitter and receiver, $\lambda_{THz}$ represents the wavelengths of the signal at the frequency $\omega_{THz}$, n and k represent the real part and the imaginary part (extinction coefficient), respectively, of the complex index of refraction of the sample in the path length L.

The receiver obtains a measurement representative of the received electric field $E_{RP}$, as shown in block 50 of FIG. 2. Similar to the transmitter 12, the receiver may comprise an electric-field detector such as a photomixer receiver (homodyne receiver). The photomixer receiver may include an antenna configured to receive the electric field and generate a corresponding voltage in response thereto, which may be directed to a high-speed photoconductor. The photoconductor is also electrically coupled to a second optical path 32 for pumping the photoconductor with beams from the same two laser sources 14a, 14b pumping the photomixer transmitter 12. In this regard, the beam combiner/splitter 16 may separate each of the signals from the laser sources into the aforementioned first optical path 18, as well as another, second optical path (e.g., optical fiber) for pumping the receiver photomixer. These signals, then, may modulate a conductance of the photomixer as described by the following:

$$G_{RP} = \eta_R E_1 E_2 \cos(\omega_{THz} t + \phi_{12R}) \quad (7)$$

where $\eta_R$ represents the photomixer receiver conversion efficiency, and $\phi_{12R} = \phi_{2R} - \phi_{1R}$, $\phi_{1R}$ and $\phi_{2R}$ representing phase constants introduced by virtue of propagation of the beams through the second optical path.

The voltage generated by the receiver antenna may be applied to the photomixer active material, and produce a current through the modulated conductance that is the product of equations (6) and (7). The difference frequency result of the product is the down-converted signal current $I_{Down}$, which may be represented as follows:

$$I_{Down} = \frac{E_{RPmp} G_{RPmp}}{2} \times e^{-2\pi k \frac{L}{\lambda_{THz}}} \times \begin{bmatrix} \cos\left(\omega_m t + \phi_T - 2\pi \frac{n \times L}{\lambda_{THz}} - \phi_{12R}\right) + \\ \cos\left(\omega_m t - \phi_T + 2\pi \frac{n \times L}{\lambda_{THz}} + \phi_{12R}\right) \end{bmatrix} \quad (8)$$

where, $$E_{RPmp} = \frac{V_m \eta_T E_1 E_2}{2} \text{ and } G_{RPmp} = \eta_R E_1 E_2$$

A corresponding down-converted electric-field (or signal) $E_R$, then, may be calculated as follows:

$$E_R = I_{Down} R_{Load} \quad (9)$$

where $R_{Load}$ represents the receiver 30 electronic load resistance. For more information on such a receiver, see the aforementioned '683 patent.

The down-converted signal current $I_{Down}$ and/or electric-field (or signal) $E_R$ may be applied to receiver signal conditioning circuitry 34 including, for example, an anti-aliasing filter 36. The output of the signal conditioning circuitry may then be input to a processor 38, such as for performing digital signal processing operations thereon. In this regard, the processor can comprise any of a number of different processing devices capable of operating in accordance with exemplary embodiments of the present invention. For example, the processor can comprise a computer (e.g., personal computer, laptop computer, server computer, workstation computer), microprocessor, coprocessor, controller, a specialized digital signal processor and/or various other processing devices including integrated circuits such as an ASIC (application specific integrated circuit), FPGA (field programmable gate array) or the like.

If the spectrometer system 10 frequency modulates (at frequency $\omega_m$) the signal, the signal processing operations performed by the processor 38 may include recovering the amplitude of the down-converted signal $E_R$ such as by an analog-to-digital converter (A/D) 39 direct sampling of the signal at the modulating frequency $\omega_m$, and the processor Discrete Fourier Transformation (DFT) processing of the sampled data. Alternatively, for example, the spectrometer system may further include a synchronous demodulator such as a lock-in amplifier (not shown) for further processing the down-converted signal $E_R$. In this regard, such a synchronous demodulator may include a local oscillator operating at the modulating frequency $\omega_m$ to thereby recover the amplitude of the down-converted signal.

In operation as a spectrometer, the system 10 scans through a number of transmission frequencies in a range of frequencies, such as by pumping the photomixers of the transmitter 12 and receiver 30 with tunable laser sources at frequency $\omega_2$, and frequency $\omega_1$ that are scanned through a number of frequencies, as shown in blocks 54 and 56 of FIG. 2. For each transmission frequency in the range of frequency, and thus each beam of radiation having a different transmission frequency, the processor 38 may measure the amplitude and/or phase of the down-converted signal current $I_{Down}$. The resulting collection of transmissions amplitudes and/or phases, and associated transmission frequencies, may define a measured absorption or dispersion signature for the sample in the sample cell 26, from which the sample may be identified, as shown in block 58 of FIG. 2.

As explained in the background section, in certain optical transmission systems (e.g., spectrometer systems), spurious thermal and mechanical disturbances may undesirably generate variations in path length that modulate the received field phase and down-converted amplitude. Exemplary embodiments of the present invention therefore provide an apparatus and method of modulating the path length of either or both of the first or second optical paths 18, 32 to at least partially reject path length instabilities that may produce transmitted signal amplitude errors. The applied path length modulation may allow recovery of the transmitted signal amplitude during a relatively short dwell time of the measurement of each spectral point (selected frequency) of the scanning spectrometer. In this regard, phase modulation by spurious path variations may be mitigated through the intentional path stretching that spans multiple waves of the transmitted frequency. And with multiple wave modulation, the full amplitude of the transmitted signal may be observed and errors in signal amplitude may be suppressed.

According to exemplary embodiments, the spectrometer system 10 further includes a path length modulation arrangement 40 along either the first optical path or the second optical path, or as shown, or along each of the first and second optical paths. Exemplary embodiments may apply path length modulation to either or both of the optical paths, and in equal or differing amounts, to thereby effectuate a total system path length stretch. In this regard, when simultaneously applying modulation to both of the optical paths, the resulting system path modulation or stretch may correspond to the difference of the modulation applied to the first and second optical paths, and may require contraction (decreasing the length) of one of the paths as the other path is stretched (increasing the length).

The path length modulation arrangement 40 may comprise any of a number of apparatuses configured to dynamically stretch or contract an optical path length. In one exemplary embodiment in which an optical path includes an optical fiber, the path length modulation arrangement may comprise a spool about which the fiber may be wound, and an actuator (e.g., piezoelectric actuator) coupled to the spool configured to stretch the diameter of the spool and thus the length of the fiber wound thereabout. In such instances, contraction of the optical fiber may be effectuated by reducing a previously-applied stretch to the spool and thus the fiber.

According to exemplary embodiments of the present invention, then, before the laser sources 14a, 14b pump the photomixer transmitter 12 to thereby transmit a beam of radiation at a selected frequency (see FIG. 2, block 48), a path length rate scale factor $S_F$ may be selected, such as by the processor 38, as shown in block 46 of FIG. 3. The path length rate scale factor represents the rate of applying a system stretch (stretch of one or both optical paths, or stretch of one path coupled with contraction of the other path) during the dwell time at each frequency sample point of the scanned spectrum (i.e., the amount of time the system operates at each frequency sample point before moving to the next point).

The path length rate scale may be selected in any of a number of different manners to effectuate a desired path length modulation, such as in a manner so as to span one or more waves of the pump signal (at the difference frequency) within the optical paths 18, 32 over the dwell time at each frequency sample. More particularly, for example, the path length rate scale may be selected as an integer multiple of the period of the pump signal, such as in accordance with the following:

$$S_F = \frac{a\lambda_{THz}}{D} \tag{10}$$

where a represents a selectable integer multiple (e.g., 3), $\lambda_{THz}$ represents the wavelength of the pump signal at the difference frequency, and D represents the dwell time (e.g., 0.03 sec.). Written in terms of the difference frequency $f_{THz}$, the path length rate scale may be selected as follows:

$$S_F = \frac{a}{D} \frac{c}{f_{THz} n_F} \tag{11}$$

where $n_F$ represents the index of refraction of the propagating medium of the optical path (e.g., approximately 1.5 for optical fiber). Consider for example, an instance in which a=3, D=0.03 s, $f_{THz}$=650 GHz, and $n_F$=1.5. In such an instance, given c=3×10$^8$ m/s, the path length rate scale factor $S_F$ may be selected as approximately 30.77 mm/s.

As relatively low frequencies of the path length modulation may result in increased noise in the spectrometer system 10, before, as or after the path length rate scale factor is selected, a transmitter modulating frequency $\omega_m$ may be selected so as to elevate the signal carrier above the 1/f noise region of the receiver electronics, as shown in block 44. This selection of the modulating frequency may permit the system to at least partially avoid increased noise at relatively low frequencies of the path length modulation. The transmitter modulating frequency may be selected in a number of different manners, such as from analysis of a measured noise density spectrum of the receiver. One example of a measured noise density spectrum is shown in the graph of FIG. 4. As shown, the 1/f noise region of the receiver electronics is at approximately 1 kHz. And from this exemplary noise density spectrum, it may be shown that a transmitter modulation frequency $\omega_m$ at or above 10 kHz may be needed to at least partially avoid excess 1/f noise.

Having selected the path length rate scale factor $S_F$ and transmitter modulating frequency $\omega_m$, the method may proceed similar to before, including transmitting a beam of radiation (i.e., source beam) at a selected transmission frequency, as shown in block 48 of FIG. 3. As the beam of radiation is transmitted during the dwell time of the selected transmission frequency, the processor 38 may control the path length modulation arrangement(s) 40 (or more particularly, for example, the actuator(s) of the arrangements) to stretch and/or contract the first optical path 18 and/or the second optical path 32 to effectuate a total system path length stretch. In such an instance, the emitted signals $E_{\omega 1}$ and $E_{\omega 2}$ may be represented as follows:

$$E_{\omega 1}=E_1 \cos(\omega_1 t + \omega_{FS} t + \phi_{1T}) \quad (12)$$

$$E_{\omega 2}=E_2 \cos(\omega_2 t + \omega_{FS} t + \phi_{2T}) \quad (13)$$

The difference (i.e., transmission) frequency (i.e., $\omega_2 - \omega_1$) in the photocurrent induced in the diode of the transmitter 12, then, may have a corresponding electric field:

$$E_T = \eta_T E_1 E_2 \cos((\omega_{THz} + \omega_{FS})t + \phi_{12}) \quad (14)$$

where $\omega_{FS}$ represents the path length modulation frequency at the difference frequency, which may be represented as follows:

$$\omega_{FS} = \frac{2\pi}{\lambda_{THz}} n_F S_F \quad (15)$$

Similar to before, the transmitter 12 may be coupled to a transmitter bias modulator 20 including a voltage source 22 configured to generate a sinusoidal modulated voltage with which the photomixer of the transmitter may be biased, the modulator producing an electric field $E_M = V_m \cos(\omega_m t)$. The transmitted electric field, then, may be represented as the product of $E_T$ and $E_M = V_m \cos(\omega_m t)$, as follows:

$$E_{TM} = V_m \cos(\omega_m t) \eta_T E_1 E_2 \cos((\omega_{THz} + \omega_{FS})t + \phi_T) \quad (16)$$

$$E_{TM} = \frac{V_m \eta_T E_1 E_2}{2} [ \quad (17)$$
$$\cos((\omega_{THz} + \omega_{FS} + \omega_m)t + \phi_T) + \cos((\omega_{THz} + \omega_{FS} - \omega_m)t + \phi_T)]$$

The beam of radiation from the transmitter may, as before, pass through the collimating lens 24 and sample cell 26. A portion of the beam of radiation may exit the sample cell, pass through the focusing lens 28, and be picked up or otherwise received by the receiver 30, as shown at block 50; and from the received signal, the complex index of refraction of the sample may be calculated, as explained further below and as shown at block 52. This received signal $E_{RP}$ may be represented as follows:

$$E_{RP} = \frac{V_m \eta_T E_1 E_2}{2} \times e^{-2\pi k \frac{L}{\lambda_{THz}}} \times \left[ \begin{array}{l} \cos\left((\omega_{THz} + \omega_{FS} + \omega_m)t + \phi_T - 2\pi \frac{n \times L}{\lambda_{THz}}\right) + \\ \cos\left((\omega_{THz} + \omega_{FS} - \omega_m)t + \phi_T - 2\pi \frac{n \times L}{\lambda_{THz}}\right) \end{array} \right] \quad (18)$$

The receiver 30 may receive the electric field and generate a corresponding voltage in response thereto. The voltage generated by the receiver may be applied to the photomixer active material, and produce a current through the modulated conductance that is the product of equations (18) and (7). The difference frequency result of the product is the down-converted signal current $I_{Down}$, which may be represented as follows:

$$I_{Down} = \frac{E_{RPmp} G_{RPmp}}{2} \times e^{-2\pi k \frac{L}{\lambda_{THz}}} \times \left[ \begin{array}{l} \cos\left((\omega_m + \omega_{FS})t + \phi_T - 2\pi \frac{n \times L}{\lambda_{THz}} - \phi_{12R}\right) + \\ \cos\left((\omega_m - \omega_{FS})t - \phi_T - 2\pi \frac{n \times L}{\lambda_{THz}} + \phi_{12R}\right) \end{array} \right] \quad (19)$$

The corresponding down-converted electric-field (or signal) $E_R$, then, may be calculated according to the following:

$$E_R = \quad (20)$$
$$E_o \times e^{-2\pi k \frac{L_s}{\lambda_{THz}}} \times \left[ \begin{array}{l} \cos\left((\omega_m + \omega_{FS})t + \phi - 2\pi \frac{n_o \times L_R + n_s \times L_s}{\lambda_{THz}}\right) + \\ \cos\left((\omega_m - \omega_{FS})t - \phi + 2\pi \frac{n_o \times L_R + n_s \times L_s}{\lambda_{THz}}\right) \end{array} \right]$$

and may be simplified as follows:

$$E_R = E_o [\cos((\omega_m + \omega_{FS})t + \phi) + \cos((\omega_m - \omega_{FS})t - \phi)] \quad (21)$$

In the preceding equations, $L_R$ represents the propagation path length in the reference or free-space medium with free-space index of refraction $n_o$ (=1), $L_s$ represents the sample thickness of or a propagation path length through the sample medium with index of refraction $\tilde{n} = n_s + ik$ ($n_s$ and $k$ respectively representing the real and imaginary parts of the complex index $\tilde{n}$), and $E_o$ and $\phi$ may be represented as follows:

$$E_o = \frac{1}{2} E_{RPmp} G_{RPmp} R_{Load}$$

$$\phi = \phi_T - 2\pi \frac{n_o \times L_R + n_s \times L_s}{\lambda_{THz}} - \phi_{12R}$$

where $E_o$ represents a signal amplitude with no absorption (i.e., k=0). This result is the mixing product of the receiver photomixer as illustrated in the spectral diagrams of FIG. 5.

Also as before, the down-converted signal current $I_{Down}$ and/or electric-field (or signal) $E_R$ may be applied to receiver signal conditioning circuitry 34 and then input to a processor 38, and may include recovery of the amplitude of the down-converted signal $E_R$. In equations (20) and (21), the constant phase term $\phi$ may vary with path length drift as a function of temperature and mechanical disturbances. By performing path length modulation according to exemplary embodiments of the present invention, the received signal amplitude may be extracted at much higher frequencies than any path drift affecting signal phase. And from the received signal amplitude and phases, the complex index of refraction of the sample may be calculated.

More particularly, according to one exemplary embodiment of the present invention, the amplitude of the down-converted signal $E_R$ may be recovered by an analog-to-digital converter (A/D) 39 direct sampling of the signal $E_R$ at the modulating frequency $\omega_m$, and the processor Discrete Fourier Transformation (DFT) processing of the sampled data. In this regard, the sequence of sampled values of the signal output from the A/D may be represented as follows:

$$E_b = E_R(n \times \tau_s) \quad (22)$$

where b represents the index of the sampled sequence b=0, 1, 2, 3, ... B−1, B represents the number of samples, and $\tau_s$ represents a sampling time interval (in seconds) that may be selected to ensure no aliasing at $\omega_{FS}+\omega_m$.

The sequence of sampled values $E_b$ may be received by the processor 38, which may then perform DFT processing of the sampled values. Applying Euler's formula to the DFT X(f) of a complex sequence $x(n \times \tau_s)$, the DFT may be represented as:

$$X(f) = \sum_{b=0}^{B-1} x(b \times \tau_s) \times (\cos(2\pi f b \tau_s) + i\sin(2\pi f b \tau_s)) \quad (23)$$

where f represents the frequency of the sinusoid at which the DFT is evaluated (in Hz). Presuming a frequency of interest of $\omega_m-\omega_{FS}$ and setting the frequency $2\pi f=\omega_m-\omega_{FS}$, and additionally applying a normalization of 2/N, the DFT of the sampled values $E_b$ may be represented as:

$$X(f) = \quad (24)$$
$$X_{\omega_m-\omega_{FS}} = \frac{2}{B}\sum_{b=0}^{B-1} E_b \times (\cos((\omega_m - \omega_{FS})b\tau_s) + i\,\sin((\omega_m - \omega_{FS})b\tau_s))$$

The sequence of functions may be equally applied to the frequency of interest $\omega_m+\omega_{FS}$ (setting $2\pi f=\omega_m+\omega_{FS}$) to yield:

$$X(f) = \quad (25)$$
$$X_{\omega_m+\omega_{FS}} = \frac{2}{B}\sum_{b=0}^{B-1} E_b \times (\cos((\omega_m + \omega_{FS})b\tau_s) + i\,\sin((\omega_m + \omega_{FS})b\tau_s))$$

The processor 38 may calculate the amplitude and phase only for the frequency components of interest $(\omega_m-\omega_{FS})$ and $(\omega_m+\omega_{FS})$ as a function of the DFTs equations (24) and (25). These results may be complex values whose magnitudes are equal and phases are of opposite sign as indicated by equations (20) and (21). The reported, transmitted amplitude may then be calculated as the average of the above two magnitudes. Phase information may be used to derive the complex index of the medium in the propagation path. Notably, the resulting processing signal bandwidth may be limited by the transform of the rectangular window whose width may be the total sample time, i.e., $B \times \tau_s$. Windowing functions common to Fast Fourier Transform processing may be applied to manage the sidelobes and width of the processing passband.

The phase information that leads to the real part of the index of refraction (i.e., n or $n_s$) may be derived from equations (24) and (25) as follows:

$$\phi - 2\pi \frac{n \times L}{\lambda_{THz}} = \arctan\left(\frac{\sum_{B=0}^{B-1} E_b \times \sin((\omega_m + \omega_{FS})b\tau_s)}{\sum_{B=0}^{B-1} E_b \times \cos((\omega_m + \omega_{FS})b\tau_s)}\right) \quad (26)$$

Performing a similar computation using the lower sideband $((\omega_m-\omega_{FS})$ components results in the same phase value with the opposite sign, i.e., negated. The complex index of refraction of the sample in the propagation path ñ may be derived from the measured amplitude and phase expressed in equation (20) by first obtaining or otherwise retrieving (e.g., from memory embodied within or otherwise associated with the processor 38) reference measurements of the amplitude ($E_o$) and phase ($\phi_{REF}$) for a transmitted signal passing through the sample cell 26 with the base medium (e.g., ambient air) but without the sample medium. Then, with the sample medium having been inserted into the cell, and sample measurements of the amplitude ($E_s$) and phase ($\phi_{SAMPLE}$) may be obtained for a transmitted signal passing through the sample cell including the sample and base mediums. The reference and sample phases may be represented as follows:

$$\phi_{REF} = \phi - 2\pi \frac{n_o \times L_R}{\lambda_{THz}} \quad (27)$$

$$\phi_{SAMPLE} = \phi - 2\pi \frac{n_o \times (L_R - L_s) + n_s \times L_s}{\lambda_{THz}} \quad (28)$$

The reference and sample amplitudes may be represented as in equations (24) and (25), and may be averaged over the frequency components of interest $(\omega_m-\omega_{FS})$ and $(\omega_m+\omega_{FS})$ to yield:

$$E_o = \frac{|X_{\omega_m-\omega_{FS}}| + |X_{\omega_m+\omega_{FS}}|}{2}\bigg|_{REF} \quad (29)$$

$$E_s = \frac{|X_{\omega_m-\omega_{FS}}| + |X_{\omega_m+\omega_{FS}}|}{2}\bigg|_{SAMPLE} \quad (30)$$

From the preceding measurements and their representations, the real part of the index of refraction of the sample may be obtained as follows:

$$n_s = (\phi_{REF} - \phi_{SAMPLE}) \times \frac{\lambda_{THz}}{2\pi \times L_s} + n_o \quad (31)$$

Note that it may be desirable to avoid the $2\pi$ phase ambiguity that may result if $(\phi_{REF}-\phi_{SAMPLE}) > 2\pi$; and as such, a constraint may be implemented in which $L_s \times (n_s-n_o) < \lambda_{THz}$. This may not be an issue for gas samples with indices near unity, but for solids and liquids, may be accomplished by using thin samples.

The imaginary part of the index of refraction of the sample, k (i.e., the extinction coefficient) may be calculated as follows. From equation (20), and equations (29) and (30), the following relationship between the reference and sample amplitudes $E_o$ and $E_s$ may be obtained:

$$e^{-2\pi k \frac{L_s}{\lambda_{THz}}} = \frac{E_s}{E_o} \quad (32)$$

And from this expression, the extinction coefficient may be calculated as follows;

$$k = -\frac{\lambda_{THz}}{2\pi L_s} \ln\left(\frac{E_s}{E_o}\right) \quad (33)$$

Similar to before, the system 10 may scan through a number of transmission frequencies in a range of frequencies, as shown in blocks 54 and 56 of FIG. 3. As the path length rate scale factor $S_F$ may be selected as a function of the transmission frequency (see equation (11)), the path length rate scale factor may be re-selected for each transmission frequency and may differ from one transmission frequency to the next. For each transmission frequency in the range of frequency, and thus each beam of radiation having a different transmission frequency, the processor 38 may measure the amplitude and/or phase of the down-converted signal current $I_{Down}$. The resulting collection of transmissions amplitudes and/or phases, and associated transmission frequencies, may define a measured absorption or dispersion signature for the sample in the sample cell 26, from which the sample may be identified, as shown in block 58 of FIG. 3.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
a transmitter and receiver, the transmitter being configured to transmit an electromagnetic signal through a sample cell to the receiver at each of one or more selectable frequencies, the sample cell including a sample medium and a base medium, the receiver being configured to receive the electromagnetic signal and another electromagnetic signal for mixing therewith, system including a first propagation path of the electromagnetic signal to the transmitter, and a second propagation path of the other electromagnetic signal to the receiver;
an arrangement located along either of the first or second propagation paths, or along each of the first and second propagation paths, the arrangement configured to alter the length of a respective propagation path such that the difference of the lengths of the first and second propagation paths is altered at a pre-selected rate during transmission of the electromagnetic signal from the transmitter to the receiver, and receipt of the electromagnetic signal and the other electromagnetic signal at the receiver; and
a processor configured to recover an amplitude and phase of the transmitted electromagnetic signal, and configured to calculate a complex index of refraction of the sample medium as a function of the amplitude and phase of the transmitted electromagnetic signal.

2. The system of claim 1, wherein the processor being configured to recover an amplitude and phase of the transmitted electromagnetic signal includes being configured to receive a sequence of samples of the received electromagnetic signal, and Discrete Fourier Transformation process the sequence of samples.

3. The system of claim 1, wherein the processor being configured to calculate a complex index of refraction of the sample medium includes being configured to calculate a real part and an imaginary part of the complex index of refraction, the real part of the complex index of refraction being calculated as a function of the recovered phase of the transmitted electromagnetic signal, and as a function of a recovered phase of an electromagnetic signal transmitted through the sample cell including the base medium but without the sample medium.

4. The system of claim 3, wherein the processor being configured to calculate the real part of the complex index of refraction includes being configured to calculate the real part $n_s$ of the complex index of refraction according to the following:

$$n_s = (\phi_{REF} - \phi_{SAMPLE}) \times \frac{\lambda}{2\pi \times L_s} + n_o$$

where $\phi_{SAMPLE}$ represents the recovered phase of the transmitted electromagnetic signal, $\phi_{REF}$ represents the recovered phase of an electromagnetic signal transmitted through the sample cell including the base medium but without the sample medium, $\lambda$ represents the wavelength of the electromagnetic signal at a respective frequency, $L_s$ represents a propagation path length through the sample medium, and $n_o$ represents the free-space index of refraction.

5. The system of claim 1, wherein the processor being configured to calculate a complex index of refraction of the sample medium includes being configured to calculate a real part and an imaginary part of the complex index of refraction, the imaginary part of the complex index of refraction being calculated as a function of the recovered amplitude of the transmitted electromagnetic signal, and as a function of a recovered amplitude of an electromagnetic signal transmitted through the sample cell including the base medium but without the sample medium.

6. The system of claim 5, wherein the processor being configured to calculate the imaginary part of the complex index of refraction includes being configured to calculate the imaginary part k of the complex index of refraction according to the following:

$$k = -\frac{\lambda}{2\pi L_s} \ln\left(\frac{E_s}{E_o}\right)$$

where $E_s$ represents the recovered amplitude of the transmitted electromagnetic signal, $E_o$ represents the recovered amplitude of an electromagnetic signal transmitted through the sample cell including the base medium but without the sample medium, $\lambda$ represents the wavelength of the electromagnetic signal at a respective frequency, and $L_s$ represents a propagation path length through the sample medium.

7. The system of claim 1, wherein the arrangement comprises a pair of arrangements each of which is located along a respective one of the first and second propagation paths, one of the arrangements being configured to increase the length of one of the propagation paths, and the other of the arrangements being configured to decrease the length of the other of the propagation paths, such that the difference of the lengths of the first and second propagation paths is increased at the pre-selected rate.

8. The system of claim 1 further comprising:
a modulator configured to modulate the electromagnetic signal transmitted by the transmitter, the modulator being configured to modulate the electromagnetic signal at a frequency above the 1/f noise region of the receiver.

9. The system of claim 1, wherein the pre-selected rate comprises a rate $\omega_{FS}$ selected to effectuate a path length modulation at a frequency:

$$\omega_{FS} = \frac{2\pi}{\lambda} n_F S_F$$

where $\lambda$ represents the wavelength of the electromagnetic signal at a respective frequency, $n_F$ represents the index of refraction of a propagating medium of the propagation paths, and $S_F$ represents the pre-selected rate.

10. The system of claim 9 further comprising:
a modulator configured to modulate the electromagnetic signal transmitted by the transmitter, the modulator being configured to modulate the electromagnetic signal at a frequency $\omega_m$,
wherein the processor being configured to recover an amplitude and phase of the transmitted electromagnetic signal includes being configured to receive a sequence of samples of the received electromagnetic signal, and Discrete Fourier Transformation (DFT) process the sequence of samples at a first frequency of interest $\omega_m - \omega_{FS}$, and DFT process the sequence of samples at a second frequency of interest $\omega_m + \omega_{FS}$.

11. A method comprising:
selecting a rate of altering the difference of the lengths of first and second propagation paths, the first propagation path being of an electromagnetic signal to a transmitter configured to transmit the electromagnetic signal through a sample cell to a receiver, the receiver being configured to receive the electromagnetic signal and another electromagnetic signal for mixing therewith, and the second propagation path being of the other electromagnetic signal to the receiver;
transmitting the electromagnetic signal from the transmitter through a sample cell to the receiver at each of one or more selectable frequencies, and receiving the electromagnetic signal and the other electromagnetic signal at the receiver, the sample cell including a sample medium and a base medium,;
altering the length of either or both of the first or second propagation paths as the electromagnetic signal is transmitted from the transmitter to the receiver, and the electromagnetic signal and the other electromagnetic signal are received at the receiver, either or both of the propagation paths being altered such that the difference of the lengths of the first and second propagation paths is altered at the selected rate; and
recovering an amplitude and phase of the transmitted electromagnetic signal, and calculating a complex index of refraction of the sample medium as a function of the amplitude and phase of the transmitted electromagnetic signal.

12. The method of claim 11, wherein recovering an amplitude and phase of the transmitted electromagnetic signal includes receiving a sequence of samples of the received electromagnetic signal, and Discrete Fourier Transformation processing the sequence of samples.

13. The method of claim 11, wherein calculating a complex index of refraction of the sample medium includes calculating a real part and an imaginary part of the complex index of refraction, the real part of the complex index of refraction being calculated as a function of the recovered phase of the transmitted electromagnetic signal, and as a function of a recovered phase of an electromagnetic signal transmitted through the sample cell including the base medium but without the sample medium.

14. The method of claim 13, wherein calculating the real part of the complex index of refraction includes calculating the real part $n_s$ of the complex index of refraction according to the following:

$$n_s = (\phi_{REF} - \phi_{SAMPLE}) \times \frac{\lambda}{2\pi \times L_s} + n_o$$

where $\phi_{SAMPLE}$ represents the recovered phase of the transmitted electromagnetic signal, $\phi_{REF}$ represents the recovered phase of an electromagnetic signal transmitted through the sample cell including the base medium but without the sample medium, $\lambda$ represents the wavelength of the electromagnetic signal at a respective frequency, $L_s$ represents a propagation path length through the sample medium, and $n_o$ represents the free-space index of refraction.

15. The method of claim 11, wherein calculating a complex index of refraction of the sample medium includes calculating a real part and an imaginary part of the complex index of refraction, the imaginary part of the complex index of refraction being calculated as a function of the recovered amplitude of the transmitted electromagnetic signal, and as a function of a recovered amplitude of an electromagnetic signal transmitted through the sample cell including the base medium but without the sample medium.

16. The method of claim 15, wherein calculating the imaginary part of the complex index of refraction includes calculating the imaginary part k of the complex index of refraction according to the following:

$$k = -\frac{\lambda}{2\pi L_s} \ln\left(\frac{E_s}{E_o}\right)$$

where $E_s$ represents the recovered amplitude of the transmitted electromagnetic signal, $E_o$ represents the recovered amplitude of an electromagnetic signal transmitted through the sample cell including the base medium but without the sample medium, $\lambda$ represents the wavelength of the electromagnetic signal at a respective frequency, and $L_s$ represents a propagation path length through the sample medium.

17. The method of claim 11, wherein altering the length comprises increasing the length of one of the propagation paths, and decreasing the length of the other of the propagation paths, such that the difference of the lengths of the first and second propagation paths is increased at the selected rate.

18. The method of claim 11 further comprising:
modulating the electromagnetic signal transmitted by the transmitter, the electromagnetic signal being modulated at a frequency above the 1/f noise region of the receiver.

19. The method of claim 11, wherein selecting a rate comprises selecting a rate $\omega_{FS}$ to effectuate a path length modulation at a frequency:

$$\omega_{FS} = \frac{2\pi}{\lambda} n_F S_F$$

where $\lambda$ represents the wavelength of the electromagnetic signal at a respective frequency, $n_F$ represents the index of refraction of a propagating medium of the propagation paths, and $S_F$ represents the selected rate.

20. The method of claim 19 further comprising:

modulating the electromagnetic signal transmitted by the transmitter, the electromagnetic signal being modulated at a frequency $\omega_m$, wherein recovering an amplitude and phase of the transmitted electromagnetic signal includes receiving a sequence of samples of the received electromagnetic signal, and Discrete Fourier Transformation (DFT) processing the sequence of samples at a first frequency of interest $\omega_m - \omega_{FS}$, and DFT processing the sequence of samples at a second frequency of interest $\omega_m + \omega_{FS}$.

* * * * *